(12) United States Patent
Irish et al.

(10) Patent No.: US 9,924,921 B1
(45) Date of Patent: Mar. 27, 2018

(54) SYSTEM FOR MAPPING JOINT PERFORMANCE

(71) Applicant: QUALCOMM Incorporated, San Diego, CA (US)

(72) Inventors: Linda Irish, San Diego, CA (US); William Henry Von Novak, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/628,428

(22) Filed: Jun. 20, 2017

(51) Int. Cl.
*A61B 7/04* (2006.01)
*A61B 5/00* (2006.01)
*A61B 5/11* (2006.01)

(52) U.S. Cl.
CPC .............. *A61B 7/04* (2013.01); *A61B 5/1114* (2013.01); *A61B 5/4528* (2013.01); *A61B 5/7282* (2013.01); *A61B 2562/0204* (2013.01)

(58) Field of Classification Search
None
See application file for complete search history.

(56) References Cited

U.S. PATENT DOCUMENTS

| 4,836,218 A | 6/1989 | Gay et al. |
| 7,328,131 B2 | 2/2008 | Donofrio et al. |
| 8,025,632 B2 * | 9/2011 | Einarsson .......... A41D 13/1281 602/23 |
| 8,864,686 B2 | 10/2014 | Roche et al. |
| 9,101,394 B2 | 8/2015 | Arata et al. |
| 2016/0302721 A1 | 10/2016 | Wiedenhoefer et al. |
| 2016/0324487 A1 * | 11/2016 | Guo .................... G08B 21/0269 |
| 2017/0000386 A1 * | 1/2017 | Salamatian ............ A61B 5/742 |

\* cited by examiner

*Primary Examiner* — Paul Huber
(74) *Attorney, Agent, or Firm* — Kilpatrick Townsend & Stockton

(57) ABSTRACT

Disclosed herein are techniques for joint performance monitoring and diagnosis. A joint monitoring system includes a plurality of event detection sensors configured to be mounted on a wearer of the joint monitoring system, and a plurality of position tracking sensors configured to be mounted on the wearer. The plurality of event detection sensors is configured to generate detection signals for detecting an event in a joint region. The joint region includes a region within a body of the wearer and within a threshold distance of a joint. The detection signals from the plurality of event detection sensors includes information for determining a location of the event. The plurality of position tracking sensors is configured to record position information of one or more body parts associated with the joint in response to the detected event.

32 Claims, 10 Drawing Sheets

SYSTEM FOR MAPPING JOINT PERFORMANCE

BACKGROUND

A complex ball joint, such as a hip joint, may have several degrees of freedom and may support the entire body weight and/or extra loading on the body. Symptoms, such as pain, discomfort, or snapping or popping sounds, may occur spontaneously when a joint does not function correctly during exercise or other daily activities. Some symptoms may not occur at the time the joint is examined, but may only occur during or after extensive physical activities and/or heavy loading. Medical imaging techniques, such as X-ray, magnetic resonance imaging (MRI), or computerized tomography (CT) scan, may not always reveal the source of the symptom. Without accurate diagnosis and identification of the source of the symptom, a joint that does not function properly may not receive an appropriate treatment.

BRIEF SUMMARY

Techniques disclosed herein relate to monitoring the range of motion of a joint (e.g., a hip joint) and the sources of defects of the joint when abnormal symptoms occur, and creating a map of defects that occurred as the joint goes through the range of motion during daily activities or medical examinations.

In accordance with an example implementation, a joint monitoring system may include a plurality of event detection sensors configured to be mounted on a wearer of the joint monitoring system and configured to generate detection signals for detecting an event in a joint region. The detection signals from the plurality of event detection sensors may include information for determining a location of the event. The joint region may include a region within a body of the wearer and within a threshold distance of a joint. The joint monitoring system may also include a plurality of position tracking sensors configured to be mounted on the wearer and configured to record position information of one or more body parts associated with the joint in response to the detected event.

In some embodiments, the joint monitoring system may further include a controller configured to execute instructions to determine the location of the event based on the detection signals from the plurality of event detection sensors. The controller may be configured to execute instructions to detect the event based on the detection signals from the plurality of event detection sensors and one or more threshold values. The controller may be configured to determine that the event detected by the plurality of event detection sensors is originated within the joint region based on the determined location of the event, and, in response to determining that the event detected by the plurality of event detection sensors is originated within the joint region, trigger the plurality of position tracking sensors to record the position information of the one or more body parts.

In some embodiments, the joint monitoring system may also include a computer-readable storage medium configured to store the position information of the one or more body parts and the determined location of the event. In some embodiments, the joint monitoring system may also include a wireless communication subsystem configured to send the position information of the one or more body parts and the determined location of the event to an external device. In some embodiments, the joint monitoring system may include a user interface, where the plurality of position tracking sensors may be configured to record the position information of the one or more body parts in response to an input signal from the user interface. The input signal from the user interface may indicate that a pain has occurred in the joint region. In some embodiments, the plurality of event detection sensors and the plurality of position tracking sensors may be embedded in an article of clothing. In some embodiments, the joint monitoring system may also include a force sensor configured to be affixed to a shoe and to detect a force applied to a leg.

In some embodiments of the joint monitoring system, the plurality of event detection sensors may include a plurality of acoustic sensors, and the event may include a sound. In some embodiments, the plurality of acoustic sensors may include an array of acoustic sensors, and the joint monitoring system may include a controller that is configured to execute instructions to determine a direction of the sound based on the detection signals from the array of acoustic sensors. In some embodiments, the controller may be configured to execute instructions to determine that the sound is originated within the joint region based on the determined direction of the sound, and, in response to determining that the sound is originated within the joint region, trigger the plurality of position tracking sensors to record the position information of the one or more body parts.

In some embodiments of the joint monitoring system, the plurality of position tracking sensors may include an accelerometer, a gyroscope, a magnetic field sensor, or any combination thereof. The position information of each of the one or more body parts may include a position of each of the one or more body parts or data for determining a position of each of the one or more body parts.

In some embodiments, the joint monitoring system may further include a calibration device including a transmitter configured to generate an acoustic signal and a radio-frequency (RF) signal. A first event detection sensor of the plurality of event detection sensors may be configured to receive the RF signal at a first time instant and receive the acoustic signal at a second time instant. The time delay between the first time instant and the second time instant may indicate a distance between the transmitter of the calibration device and the first event detection sensor. In some embodiments, the calibration device may include two or more transmitters, where each transmitter of the two or more transmitters may be configured to generate an acoustic signal and an RF signal. The first event detection sensor may be configured to receive the RF signal and the acoustic signal generated by each of the two or more transmitters. A controller may be configured to determine a location of the first event detection sensor based on time instants when the RF signal and the acoustic signal generated by each of the two or more transmitters are received by the first event detection sensor.

In accordance with an example implementation, a method for monitoring a joint is provided. The method may include receiving detection signals from a plurality of event detection sensors mounted on a subject for detecting an event in a joint region, where the joint region may include a region within a body of the subject and within a threshold distance of the joint. The method may also include determining a location of the event based on the detection signals from the plurality of event detection sensors, and receiving position information of one or more body parts associated with the joint from a plurality of position tracking sensors mounted on the subject. The position information may be recorded by the plurality of position tracking sensors in response to the detected event. In some embodiments, the event may include a sound, the plurality of event detection sensors may include a plurality of acoustic sensors, and determining the location of the event may include determining a direction of the sound based on the detection signals from the plurality of acoustic sensors.

In some embodiments, the method for monitoring the joint may also include determining that the event detected by the plurality of event detection sensors is originated within the joint region based on the determined location of the event, and, in response to determining that the event detected by the plurality of event detection sensors is originated within the joint region, triggering the plurality of position tracking sensors to record the position information of the one or more body parts. The method may also include storing the determined location of the event and the position information of the one or more body parts in a computer-readable storage medium. In some embodiments, the method may also include generating at least one of a map of ranges of motion of the joint, or a map of locations of events occurred in the joint region and corresponding position information of the one or more body parts associated with the joint, based on the determined location of the event and the position information of the one or more body parts stored in the computer-readable storage medium. In some embodiments, the method may include sending the determined location of the event and the position information of the one or more body parts to an external device using a wireless communication subsystem.

In some embodiments, the method for monitoring the joint may also include receiving a user input signal from a user interface, and, in response to receiving the user input signal, recording the position information of the one or more body parts. In some embodiments, the method may further include determining a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

In accordance with another example implementation, an apparatus may be provided, which may include means for receiving detection signals from a plurality of event detection sensors mounted on a subject for detecting an event in a joint region, where the joint region may include a region within a body of the subject and within a threshold distance of a joint. The apparatus may also include means for determining a location of the event based on the detection signals from the plurality of event detection sensors, and means for receiving position information of one or more body parts associated with the joint from a plurality of position tracking sensors mounted on the subject, where the position information may be recorded by the plurality of position tracking sensors in response to the detected event.

In some embodiments, the apparatus may further include means for determining that the event detected by the plurality of event detection sensors is originated within the joint region based on the determined location of the event, and means for, in response to determining that the event detected by the plurality of event detection sensors is originated within the joint region, triggering the plurality of position tracking sensors to record the position information of the one or more body parts. In some embodiments, the apparatus may also include means for storing or sending the determined location of the event and the position information of the one or more body parts. In some embodiments, the apparatus may include means for determining a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

In accordance with yet another example implementation, a non-transitory computer-readable storage medium including machine-readable instructions stored thereon is disclosed. The non-transitory computer-readable storage medium may include instructions that, when executed by one or more processors, cause the one or more processors to receive detection signals from a plurality of event detection sensors mounted on a subject for detecting an event in a joint region, determine a location of the event based on the detection signals from the plurality of event detection sensors, and receive position information of one or more body parts associated with the joint from a plurality of position tracking sensors mounted on the subject. The joint region may include a region within a body of the subject and within a threshold distance of a joint. The position information may be recorded by the plurality of position tracking sensors in response to the detected event.

In some embodiments, the instructions may further cause the one or more processing units to determine that the event detected by the plurality of event detection sensors is originated within the joint region based on the determined location of the event, and, in response to determining that the event detected by the plurality of event detection sensors is originated within the joint region, trigger the plurality of position tracking sensors to record the position information of the one or more body parts. In some embodiments, the instructions may also cause the one or more processing units to determine a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

BRIEF DESCRIPTION OF THE DRAWINGS

Aspects of the present disclosure are illustrated by way of example. Non-limiting and non-exhaustive aspects are described with reference to the following figures, wherein like reference numerals refer to like parts throughout the various figures unless otherwise specified.

DETAILED DESCRIPTION

Several illustrative embodiments will now be described with respect to the accompanying drawings, which form a part hereof. The ensuing description provides embodiment(s) only and is not intended to limit the scope, applicability, or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

Techniques disclosed herein relate to monitoring the range of motion of a joint (e.g., a hip, an elbow, a knee, etc.) and the sources of defects of the joint when abnormal symptoms occur during daily activities or medical examinations. The monitored information can then be used to create a map of defects that occurred as the joint goes through the range of motion, which may be useful for identifying the sources of the defects and tailoring an appropriate treatment or therapy for a patient. In some embodiments, a noninvasive sensor system including event detection sensors (e.g., acoustic sensors) and position tracking sensors attached to a patient's body may be used to detect an event in the joint region (e.g., a sound generated by the joint), determine the location of the event, and record the position information of various parts of the joint at the time the event is detected and/or during daily activities. The techniques may greatly expand the capabilities of impingement tests using in clinical examinations by creating a detailed map of the range of motion of the joint, the locations where symptoms occur within the range of motion, and the locations of various parts of the joint when the symptoms occur. The sensor system may be implemented as a wearable device or embedded in an article of clothing, such as underwear or a pair of bicycle-style shorts, to record data during daily activities, without interfering with the normal activities of the patient.

I. Hip Joint

The hip joint is one of the most important and flexible joints in the human body. Functionally, the hip joint allows a very high range of motion. The ball-and-socket structure of the joint allows the femur to circumduct freely through a 360-degree circle. The femur may also rotate about 90 degrees around its axis at the hip joint. In addition to being flexible, each hip joint is capable of supporting one half of the body's weight and any other forces acting upon the body. During running and jumping, for example, the force applied to the hip joint due to the body's movement may be many times of the force exerted by the body's weight only. The hip joint is able to accommodate these extreme forces repeatedly during intense physical activities.

Figure 1B:
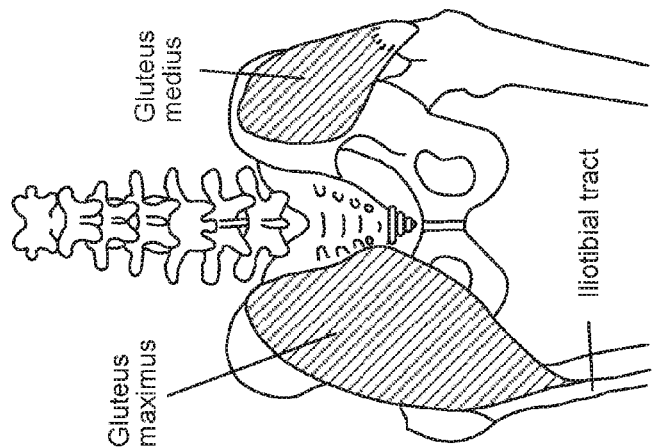
FIG. 1B is a posterior view of a hip joint.
Figure 1A:
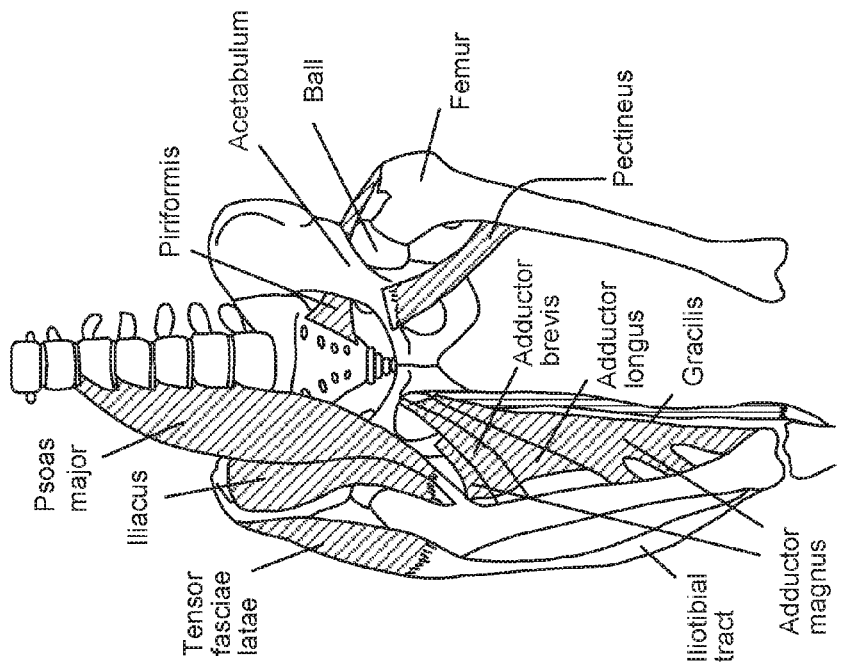
FIG. 1A is an anterior view of a hip joint.

FIG. 1A is an anterior view of a hip joint. FIG. 1B is a posterior view of a hip joint. As shown in FIG. 1A, the hip joint is a ball-and-socket synovial joint formed between the femur and the hip bone (i.e., os coax, which includes the ilium bone at the superior portion, the ischium bone at the lower posterior portion, and the pubic bone (pubis) at the lower anterior portion). A round, cup-shaped structure on the hip bone, known as the acetabulum, forms the socket for the hip joint. A rounded head of the femur forms the ball of the joint. Hyaline (articular) cartilage lines both the acetabulum and the rounded head of the femur, providing a smooth surface for the moving bones to glide past each other. Hyaline cartilage also acts as a flexible shock absorber to prevent the collision of the bones during movement. Synovial membranes between layers of the hyaline cartilage secrete (discharge) synovial fluid to lubricate the joint capsule. Surrounding the hip joint are many tough ligaments that prevent the dislocation of the joint. The strong muscles in the hip region also help to hold the hip joint together and prevent dislocation.

The muscles in the hip region provide mobility, strength, and stability to the hip joint and the bones of the hip and thigh. These muscles can be grouped into four groups based upon their locations and functions. The four groups are the anterior muscle group, the posterior muscle group, the adductor muscle group, and the abductor muscle group. The anterior muscle group includes muscles that flex (bend) the thigh at the hip. Sitting up, kicking a ball, and lifting a leg to climb a ladder are all activities that involve contraction of the anterior muscle group. The posterior muscle group includes the muscles that extend (straighten) the thigh at the hip. Climbing stairs, standing, walking, and running are all activities that require strong contractions from the posterior muscle group to extend the leg. The adductor muscle group, also known as the groin muscles, is a group located on the medial side of the thigh. These muscles move the thigh toward the body's midline. Overstretching of these muscles caused by rapid lateral movement of the thigh can lead to a groin pull, a common sports injury. The abductor muscle group is located on the lateral side of the thigh and moves the thigh away from the body's midline. Spreading the legs to do a split is an example of a movement involving the abductor muscles.

Figure 2:
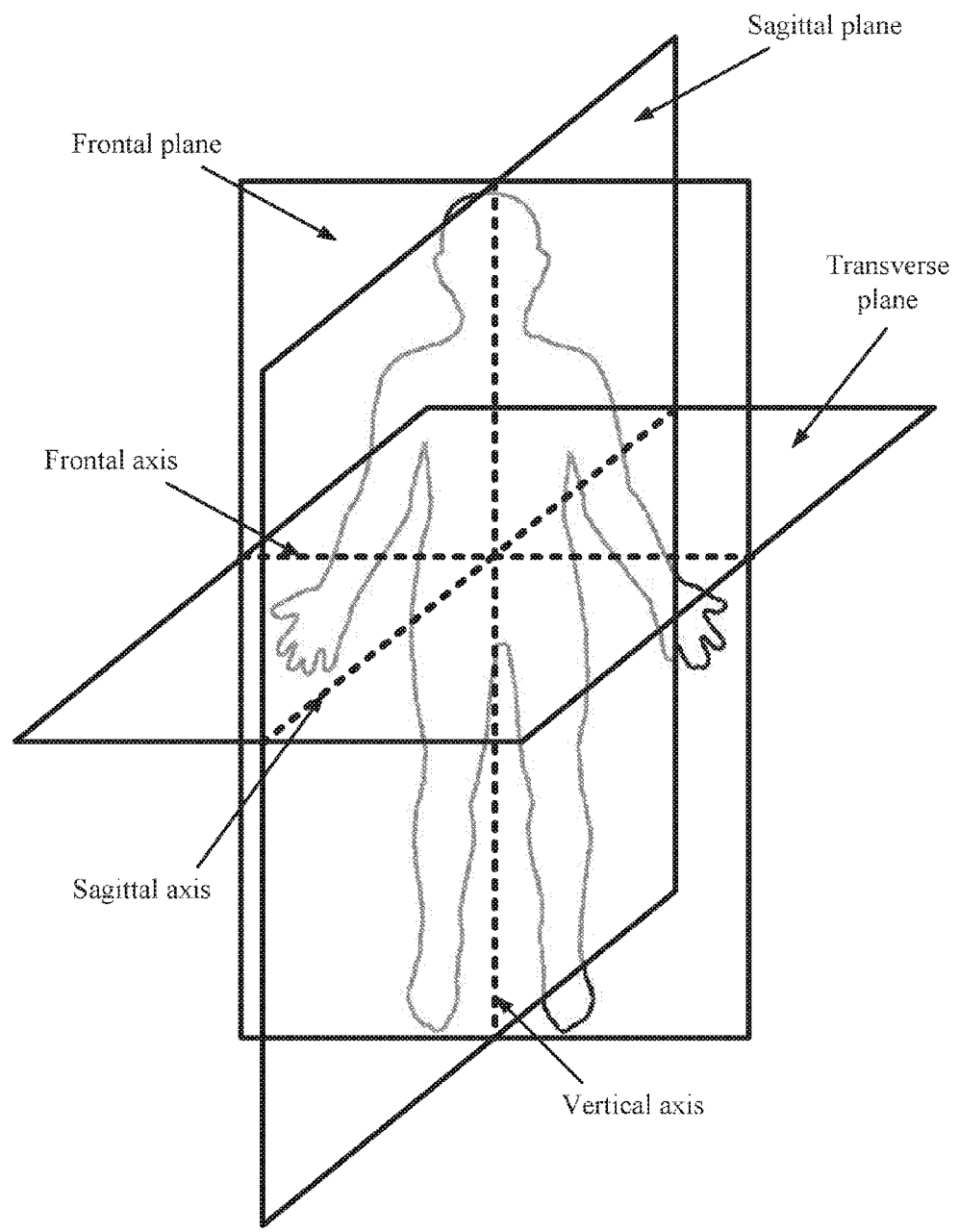
FIG. 2 illustrates main anatomical planes of motion and axes of rotation of a human body.

FIG. 2 illustrates main anatomical planes of motion and axes of rotation of a human body. The above-described hip muscles act on three mutually perpendicular main axes, all of which pass through the center of the femoral head, resulting in three degrees of freedom and three pair of principal directions: flexion and extension in a sagittal plane around a frontal axis (left-right), lateral rotation and medial rotation in a transverse plane around a longitudinal (or vertical) axis (along the thigh), and abduction and adduction in a frontal plane around a sagittal (or transverse) axis (forward-backward), and a combination of these movements (i.e. circumduction, a compound movement that defines the surface of an irregular cone).

As the hip moves in the sagittal, frontal, and transverse planes during daily activities or exercises, a click or snapping sound may occur when, for example, a chondral flap catches and releases, a muscle, tendon, or ligament rolls over a bony structure in the hip, or another event occurs. Snapping hip can occur in different areas of the hip. For example, snapping at the front of the hip may involve the hip flexor muscle rolling over the front of the hip bone, or the hip ligaments rolling over the thigh bone or tissues of the hip joint. Snapping at the side of the hip may involve the iliotibial band (ITB) rolling over the outer thigh bone (greater trochanter) or the big muscle on the back of the hip (gluteus maximus) sliding over the outer thigh bone, known as the external snapping hip syndrome. Snapping at the back of the hip may involve one of the hamstring muscles rolling over the bottom of the hip bone. Snapping hip may occur when the hip muscles are excessively used and become fatigued, tight, and/or swollen.

The iliopsoas tendon, which connects to the inner part of the upper thigh, can also snap with hip movement when the iliopsoas tendon slides over the iliopectineal eminence, known as the internal snapping hip syndrome. This typically occurs when the hip suddenly moves into extension from a flexed and externally rotated position. The iliopsoas tendon may also produce snapping with sudden movement over the anterior inferior iliac spine or possibly the bony ridge on the lesser trochanter. Less common causes of internal snapping hip syndrome include movement of the iliofemoral ligaments over the femoral head or anterior capsule of the hip.

Another site of snapping is where the ball at the top of the thigh bone fits into the socket in the pelvis to form the hip joint. The snapping may occur when the rectus femoris tendon, which runs from inside the thigh bone up through the pelvis, moves back and forth across the ball when the hip is bent and straightened. Less commonly, a cartilage tear or bits of broken cartilage or bone in the joint space can cause snapping, or a loose piece of cartilage can cause the hip to lock up. Posterior snapping hip syndrome may be caused by the movement of the long head tendon of the biceps femoris over the ischial tuberosity, and is uncommon.

Symptoms (e.g., significant pain) may occur when any bone, muscle, or ligament of a joint (e.g., the hip) does not work correctly. Medical imaging techniques, such as X-ray, magnetic resonance imaging (MRI), or computerized tomography (CT) scan, do not always reveal the source of the symptom, and some symptoms may not occur at the time the joint is examined, but may only occur during or after extensive physical activities and/or heavy loading. Locating the origin of the snapping sound and determining the magnitude of the snapping sound and/or the position of the hip along the three degrees of freedom at the time the sound occurs can be very helpful in diagnosing the hip, because these symptoms may not be observed during a physical examination or diagnosis.

Various methods may be used to evaluate a joint, such as a hip. For example, various impingement tests may be performed by bringing the joint through various positions and rotations to determine where pain may occur or where the joint may hit its limit of travel. The information from such tests may help the doctor to determine the source of the symptom, which may or may not be visible with medical imaging. However, symptoms caused by, for example, a tendon snapping over bone, chondral defects, or labrum snapping, may or may not be observed during such tests. Therefore, such tests may give a false negative for symptoms that may only occur after extensive physical activities or under heavy loading.

X-ray is a simple and cheap method of getting a two-dimensional (2-D) picture of the bony structure of the joint. When taken properly, X-ray images may reveal some defects in the hip, such as cam lesions on the femur or spacing within the joint. However, X-ray images may not show soft tissues, such as a tendon, labrum, or cartilage.

An MRI can create a three-dimensional (3-D) image that shows soft tissues. However, the resolution and contrast of the MRI image may not be sufficient to show conditions such as a torn labrum or loose cartilage. Contrast agents including Gadolinium compounds may be used to enhance the MRI image, but are generally avoided when possible due to the toxic effects of the contrast agents.

A computerized axial tomography (CAT) scan may be good for imaging bony structures, but may reveal little about soft tissues. The cost of CAT scan is much higher than X-ray, and the patient under a CAT scan may be subjected to a larger dose of radiation.

Arthroscopic surgery may give a better view of the soft tissues than the above methods, and may often take care of the defects in the joint at the time they are discovered. However, as a method of evaluation, it is very expensive and invasive.

II. Sensor System

Techniques disclosed herein relate to monitoring the range of motion of a joint, such as a hip, and creating a map of defects that occurred as the joint goes through the range of motion during daily activities or medical examinations. A noninvasive sensor system including event detection sensors (e.g., acoustic sensors) and position tracking sensors attached to a patient's body may be used to detect an event occurred in the joint region (e.g., a sound generated by the joint), determine the location of the event, and record the position information of various parts of the joint at the time the sound is detected and/or during daily activities. The techniques may greatly expand the capabilities of impingement tests by creating a detailed map of the range of motion of the joint, the locations where symptoms occur within the range of motion, and the locations of various parts of the joint when the symptoms occur.

The sensor system may be implemented as a wearable device, such as underwear or a pair of bicycle-style shorts, to record data during daily activities without interfering with the normal activities of the patient. In some examples, the sensor system may be implemented as a brace or a bandage tape that may be wrapped wound a user's body part (e.g., hip, elbow, shoulder, neck, wrist, knee, etc.), for monitoring the body part, as well as providing support for the body part.

Additionally or alternatively, the techniques may be used to monitor the progress of the healing of a body part. For example, the sensor system (e.g., in the form of a brace) may be used to measure the intensity level of snapping overtime to determine how well the injured elbow is healing. If no snapping has been detected for certain period of time, the sensor system may provide notification that the patient no longer needs to wear the brace.

Figure 3:
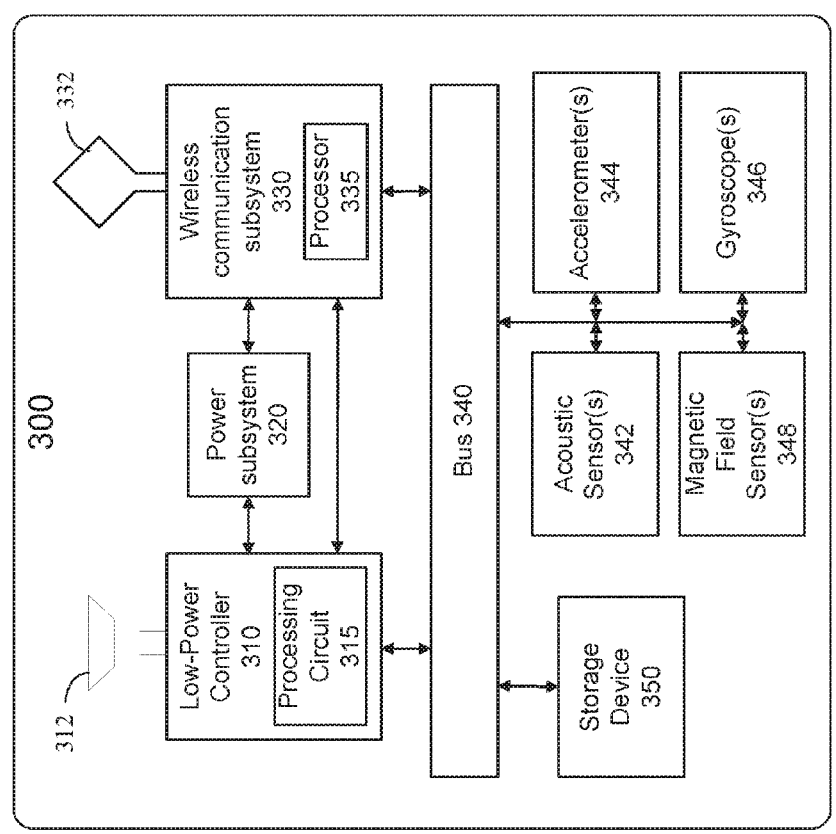
FIG. 3 illustrates a simplified block diagram of an example electronic joint monitoring system, according to certain aspects of the present disclosure.

FIG. 3 is a simplified block diagram of an example electronic joint monitoring system 300, according to certain aspects of the present disclosure. Electronic joint monitoring system 300 may include a low-power controller 310 for controlling the operations of a power subsystem 320, a wireless communication subsystem 330, a storage device 350, and various sensors including event detection sensors and position tracking sensors.

Power subsystem 320 may include one or more rechargeable or non-rechargeable batteries, such as alkaline batteries, lead-acid batteries, lithium-ion batteries, zinc-carbon batteries, and NiCd or NiMH batteries. Power subsystem 320 may also include one or more power management circuits, such as voltage regulators, DC-to-DC converters, wired (e.g., universal serial bus (USB) or micro USB) or wireless (NFC or Qi) charging circuits, energy harvest circuits, etc. In some embodiments, power subsystem 320 may include a real-time clock using, for example, a watch crystal or other crystals.

Wireless communication subsystem 330 may include a processor 335 and one or more of a cellular communication subsystem, a Global Navigation Satellite System (GNSS) (e.g., Global Positioning System (GPS)) communication subsystem, a wireless local area network (WLAN) (e.g., Wi-Fi) transceiver, a wireless wide-area network (WWAN) (e.g., CDMA or LTE.) transceiver, a Bluetooth, Bluetooth low energy (BLE), or ZigBee transceiver, or other wireless communication subsystems, such as a near-field communication (NFC) subsystem. Wireless communication subsystem 330 may be connected to or include one or more antennas 332, such as a printed antenna (e.g., a microstrip or patch antenna) or antenna array. Wireless communication subsystem 330 may be operable to be powered on, powered off, or in a standby (i.e., sleep) mode. Wireless communication subsystem 330 may be used to communicate with other devices for data transferring. In some instances, wireless communication subsystem 330 may be used to determine a location of electronic joint monitoring system 300 using, for example, the GPS communication subsystem.

Electronic joint monitoring system 300 may include various sensors, such as, for example, acoustic sensor(s) 342, accelerometer(s) 344, gyroscope(s) 346, and magnetic field sensor(s) 348. Electronic joint monitoring system 300 may also include other sensors (not shown in FIG. 3), such as proximity sensor(s), temperature sensor(s), humidity sensor(s), biometric sensor(s), motion sensor(s), etc. Acoustic sensor(s) 342 may be used to detect a snapping sound occurring in the joint region and/or to determine the location of the origin of the snapping sound. As used herein, a joint region may refer to a region within a body of a wearer of the electronic joint monitoring system and within a threshold distance of a joint, such as the hip joint. The threshold distance may be different for different joints, and may be adjusted based on the wearer of the electronic joint monitoring system. Sensors, such as accelerometer(s) 344, gyroscope(s) 346, magnetic field sensor(s) 348, optical sensor(s), ultrasonic sensor(s), barometer pressure sensor(s), or any combination thereof, may be used to determine or track the positions of different body parts associated with the joint. The sensors may be provisioned by the wearer or a medical personnel after electronic joint monitoring system 300 is attached to the wearer. For example, after electronic joint monitoring system 300 is attached to a wearer's hip, the medical personnel may specify the hip as the body part that electronic joint monitoring system 300 is attached to, and specify corresponding muscles to be monitored by the sensors.

Other sensors, such as temperature sensors and humidity sensors, may be used to monitor the condition of the environment, which may affect the performance of the joint. In some instances, biometric sensors, such as fingerprint sensor(s), may be used to identify the user. In some instances, proximity sensors may be used to determine whether electronic joint monitoring system 300 is closely affixed to a body. In some cases, a low-power motion sensor may be used and may be always powered on, and other sensors and circuits of electronic joint monitoring system 300 may be turned off after no motion has been detected for a certain period of time and may only be turned on after a motion is detected by the low-power motion sensor. For example, most circuits of electronic joint monitoring system 300 may be turned off when the user is asleep or when electronic joint monitoring system 300 is not being attached to the user. In some implementations, sensors, such as one or more optical sensors or ultrasonic sensors, may be used to identify muscle vibrations that may be caused by a joint snap to detect the joint snap and trigger the position determination.

Electronic joint monitoring system 300 may comprise one or more of the above-described sensors, which may be implemented using various technologies known to a person skilled in the art. Acoustic sensor(s) 342 may include, for example, a condenser or capacitive microphone using silicon diaphragms, a piezoelectric acoustic sensor, or an electret microphone. Accelerometer(s) 344 may be implemented using piezoelectric, piezo-resistive, capacitive, or micro electro-mechanical systems (MEMS) components. Accelerometer(s) 344 may include a two-axis or multiple-axis accelerometer. Gyroscope(s) 346 may include, for example, MEMS gyroscopes, solid-state ring laser gyroscopes, fiber optic gyroscopes, and quantum gyroscopes. Magnetic field sensor(s) 348 may include, for example, MEMS-based magnetic field sensors, or sensors based on magneto-resistive effect of thin film permalloy.

Low-power controller 310 may receive information collected by the various sensors and determine, using a processing circuit 315, whether a snapping sound has been detected, and whether and when to activate or deactivate other sensors or circuits to record the positions of various body parts associated with the joint. Processing circuit 315 may also determine the location of the origin of the snapping sound based on the amplitude and/or phase information of the acoustic signals detected by the acoustic sensors. Processing circuit 315 may include a processor (e.g., ARM® or MIPS® processor), a microcontroller, or an application specific integrated circuit (ASIC).

In some implementations, electronic joint monitoring system 300 may also include a speaker 312, which may be controlled by low-power controller 310 to generate an alarm or other signaling sounds. Alternatively or additionally, in some implementations, a photodiode or a light-emitting diode (LED) (not shown) may be used and controlled by low-power controller 310 to generate a signaling light beam.

Low-power controller 310 may include a datalogger, which may save the information detected by the various sensors to a storage device 350 when, for example, a snapping sound is detected. Storage device 350 may include, for example, a flash memory. In some instances, the datalogger may also record the time when a sound is detected.

It is noted that the embodiments of electronic joint monitoring system described in FIG. 3 are for illustration purposes only and are not meant to be limiting. Many components or modules may be omitted in FIG. 3 in order not to obscure the features being described herein. One skilled in the relevant art will appreciate that the disclosed illustrative components are not meant to be an exhaustive identification of all the components required by or present in an electronic joint monitoring system. Rather, illustrative components have been identified, in a non-limiting manner, to facilitate illustration of one or more aspects of the present disclosure. Furthermore, some components may be combined or implemented on a same circuit or device.

In some embodiments, the sensors in an electronic joint monitoring system, such as electronic joint monitoring system 300, may be placed at different body parts in the joint region. In some embodiments, electronic joint monitoring system 300 may be a body-worn system or an article of clothing. For example, in some implementations, the sensors may be embedded in different portions of a long pair of bicycle-style shorts that extend to the knee.

A. Event Detection Sensors

As described above, the electronic joint monitoring system may include event detection sensors to detect events occurred within the joint region, such as snapping sounds, other sounds, or other abnormal events. For example, acoustic sensors may be used to detect a snapping sound occurring in the joint region and/or determine the location of the snapping sound. In some implementations, the acoustic sensors may be individually positioned, while in some other implementations, the acoustic sensors may be arranged in a phased array. In some implementations, each acoustic sensor may have an independent time base. In some implementations, the acoustic sensors may be synchronized. For example, the acoustic sensors may all use a same master clock as the reference clock. In some implementations, the acoustic sensors may be mounted on, for example, a belt, bandage wrap, brace, or in a bicycle-style shorts, as described above. The acoustic sensors may also be mounted at various random locations of a patient's body near the hip.

In some cases, there may be several inches of separation between the hip joint and the locations where the muscles or tendons may snap over bony protrusions. A phased acoustic sensor array or an array of acoustic sensors with known relative phase differences may be used to detect a sound generated by the joint, such as a snapping sound, and determine the location of the source of the sound. For example, when a sound is received by the acoustic sensors, the relative phases and/or magnitudes of the signals detected by different acoustic sensors and the relative locations of the different acoustic sensors may be recorded and used to determine the approximate location where the sound is generated. The relative phases and/or magnitudes of the signals detected by the sensors and/or the determined approximate location where the sound is generated may be recorded and stored in a computer-readable storage medium, such as a flash memory.

Figure 4:
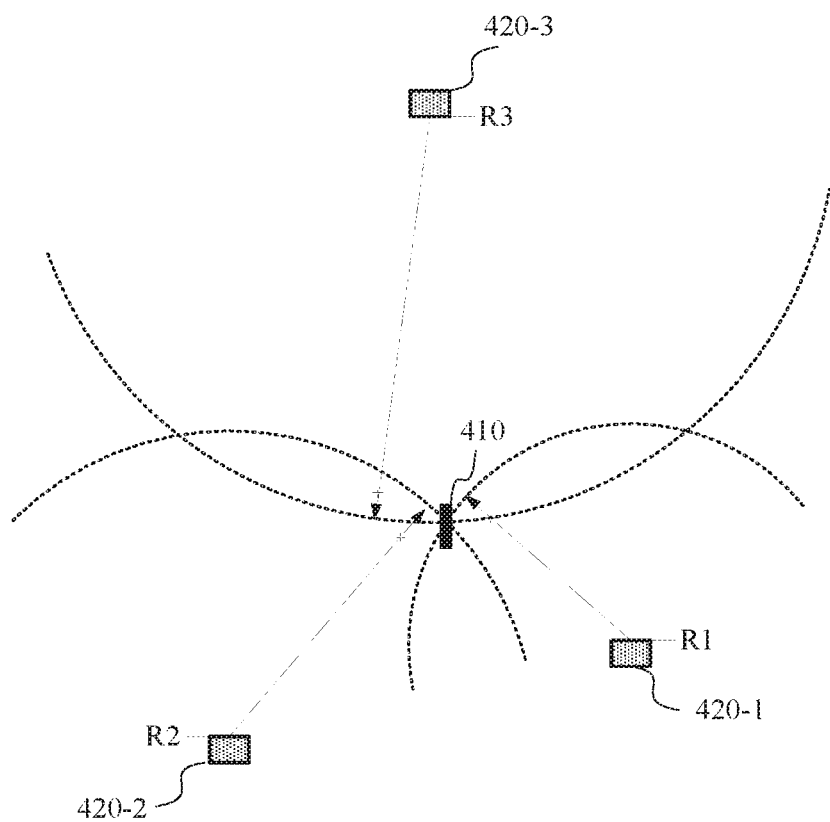
FIG. 4 illustrates an example technique for determining the location of the origin of a sound generated in a joint region, according to certain aspects of the present disclosure.

FIG. 4 illustrates an example technique for determining the location of the origin 410 of a sound generated in a joint region, according to certain aspects of the present disclosure. When a snapping sound is generated from origin 410 of the sound in the joint region, the exact location of origin 410 of the sound in the joint region may be determined using, for example, a trilateration technique. Three acoustic sensors 420-1, 420-2, and 420-3 may each receive the sound generated at origin 410 of the sound. Based on the relative phase of the sound signal detected by each of the three acoustic sensors and the speed of sound within a body, a relative distance between each sensor and origin 410 of the sound may be determined. Alternatively, the relative distance between each sensor and origin 410 of the sound may be determined based on the relative amplitude of the sound signal detected by each of the three acoustic sensors and the attenuation of sound signal as a function of propagation distance within the body. An absolute distance between each acoustic sensor and origin 410 of the sound, R1, R2, or R3, may be determined based on the known distances between the acoustic sensors. The location of origin 410 of the sound is thus the intersection point of three circles, a first circle centered at acoustic sensor 420-1 with a radius of R1, a second circle centered at acoustic sensor 420-2 with a radius of R2, and a third circle centered at acoustic sensor 420-3 with a radius of R3. Based on the know locations of the acoustic sensors and the distance between each acoustic sensor and origin 410 of the sound, the location of origin 410 of the sound may be determined. The determined location of the origin of the sound generated by the joint may then be used to determine, for example, which bone, tendon, cartilage, muscle, ligament, or other tissue has defects or has been injured, based on the anatomy of the patient's joint, which may be acquired through medical imaging, such as X-ray, MRI, or CT scan.

In some implementations, multiple phased acoustic sensor arrays may be used, where each phased acoustic sensor array may be placed at one location in the joint region. A phased acoustic sensor array may be used to more accurately determine the direction of the origin of the sound with respect to the phased acoustic sensor array.

Figure 5:
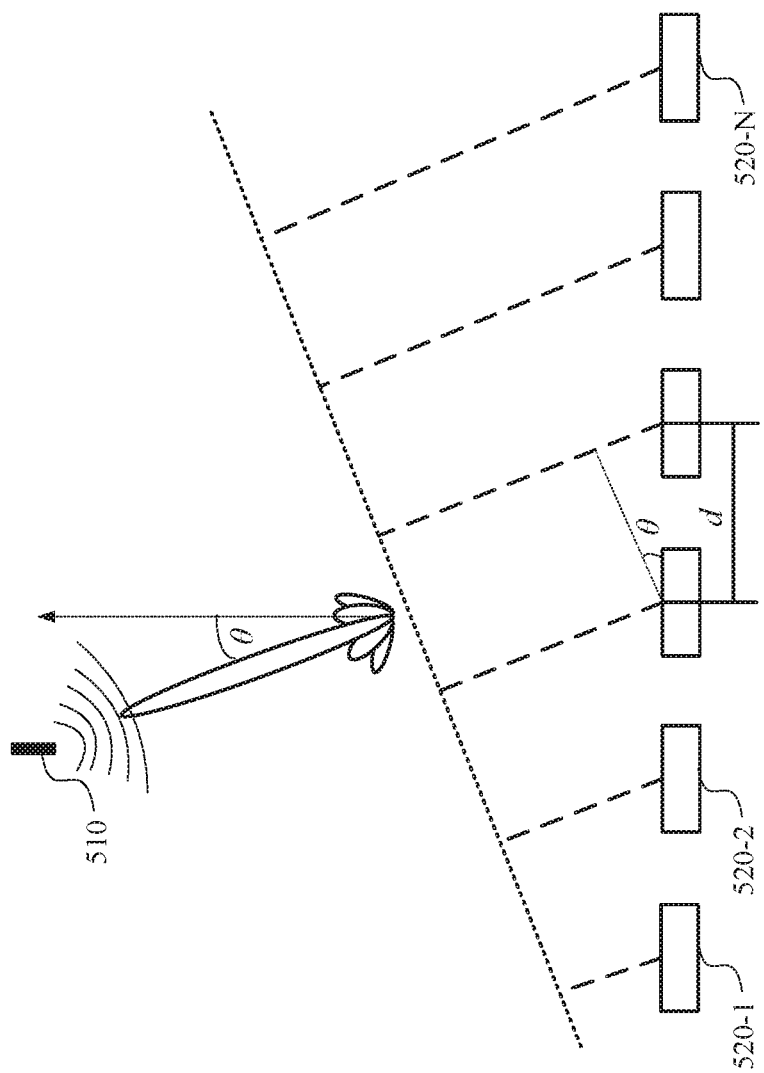
FIG. 5 illustrates an example technique for determining the direction of a sound generated in a joint region, according to certain aspects of the present disclosure.

FIG. 5 illustrates an example technique for determining the direction of a sound generated in a joint region, according to certain aspects of the present disclosure. As shown in FIG. 5, a sound is generated at an origin 510 in the joint region. The sound generated at origin 510 is detected by a plurality of acoustic sensors 520-1, 520-2, ..., and 520-N (collectively 520), where the plurality of acoustic sensors are synchronized and arranged at known locations, such as in a linear array. As such, the plurality of acoustic sensors may receive the sound signal at different times and generate detection signals with different phases. The time or phase differences among the detection signals from the plurality of acoustic sensors may depend on the distance d between adjacent acoustic sensors of the plurality of acoustic sensors and the direction θ of origin 510 with respect to the plurality of acoustic sensors. Based on the difference in the phase (or time) delay between the detection signals from adjacent acoustic sensors, the direction θ of origin 510 with respect to the plurality of acoustic sensors may be determined.

When a sound is detected, the electronic joint monitoring system may filter noises from the detected sound signal, and differentiate a sound that is generated outside of a body from a sound that is generated inside the body based on, for example, the determined direction of the origin of the sound or the determined location of the origin of the sound. If the electronic joint monitoring system determines that a detected sound is generated inside the body in the region of the joint, other sensors, such as the position tracking sensors described above with respect to FIG. 3, in the electronic joint monitoring system may be activated to determine the positions of different body parts at the time the sound is detected. If the electronic joint monitoring system determines that a detected sound is generated outside of the body, the electronic joint monitoring system may determine that the sound is not of interest and would not activate other sensors in the electronic joint monitoring system.

In some embodiments, the directions of the origin of the sound with respect to multiple phased acoustic sensor arrays may be used to determine the location of the origin of the sound, using, for example, triangulation techniques. The determined location of the origin of the sound may then be used to determine whether other sensors should be triggered.

B. Position Tracking Sensors

The position tracking sensors may be used to generate sensor data associated with the position of the joint, such as the hip, in the sagittal, frontal, and transverse planes. The position tracking sensors for determining the position of the hip along the three planes may include, for example, accelerometers, magnetic field sensors, gyroscopes, and/or barometer pressure sensors as described above. The position tracking sensors may be used in multiple locations for position sensing. For example, some position tracking sensors may be placed on predetermined locations on body parts, such as the knee, thigh, or small of the back of a person. In some embodiments, the position tracking sensors may determine the positions of the body parts that the position tracking sensors are attached to. In some embodiments, the position tracking sensors may generate sensor data for determining the positions of the of body parts by another device, such as processing circuit 315 of low-power controller 310.

Various known methods may be used by a position tracking sensor to determine its relative or absolute position and thus the position of the body part that the position tracking sensor is attached to. For example, in some implementations, each sensor may determine its own positions during motions of the joint based on, for example, the earth's magnetic field or gravity. In some implementations, each sensor may broadcast a signal or generate a modulated magnetic field such that other sensors may determine the relative position of the sensor. With some sensors placed on predetermined locations on, for example, the knee, thigh, or small of the back of a person, the position of the hip may be determined. Thus, when an acoustic event (e.g., a snapping sound) occurs, the position of the hip along the three degrees of freedom may be recorded by the position tracking sensors and stored in a storage medium, such as a flash memory.

In some instances, some snapping of the joints during daily activities, even some extreme cases of joint snapping, may be normal. Thus, a joint snapping may only be problematic if it results in pain. As such, in some cases, a patient may trigger the data collection by pushing a button (or other user interface) only when a pain occurs. For example, an application software may run on a mobile device, and the patient may trigger the data collection through the user interface of the application software and the wireless communication subsystems of the mobile device and the electronic joint monitoring system. In some cases, data from the sensors may be sent to a mobile device (e.g., a smartphone or tablet) through, for example, the wireless communication subsystem, a patient may then indicate at what point in the range of motion a pain does occur, and the associated data may then be saved to the mobile device.

C. Force Sensors

In some embodiments, one or more force sensors, such as 3 or 4-axis force sensors, may be mounted in, for example, the sole of a shoe to log force applied to the leg. The 4 axes may include X, Y, Z (weight), and rotation. For example, the force being sensed may deform a strain gauge of the force sensor, which may convert the deformation (strain) to an electrical signal. The force sensor may be used to detect and log force or torque applied to the legs during daily activities. The force sensor may also be used to detect and log the force or torque applied to the legs of a patient by a doctor during a physical examination, for example, to determine the range of movement of the hip, the force needed to move the hip to a certain range, or forces that may cause pain in the hip.

III. Positioning of the Sensors

Because the gait information collected is determined based on the location of each sensor, such as the placement location of the sensors on the body and the locations of the sensors during the motions of the joint, it is desirable to place the sensors at appropriate locations and correctly determine the locations of the sensors during the motions, such that the location of the source of sound generated by the joint and/or relative movement of the body parts where the sensors are placed may be determined.

Figure 6:
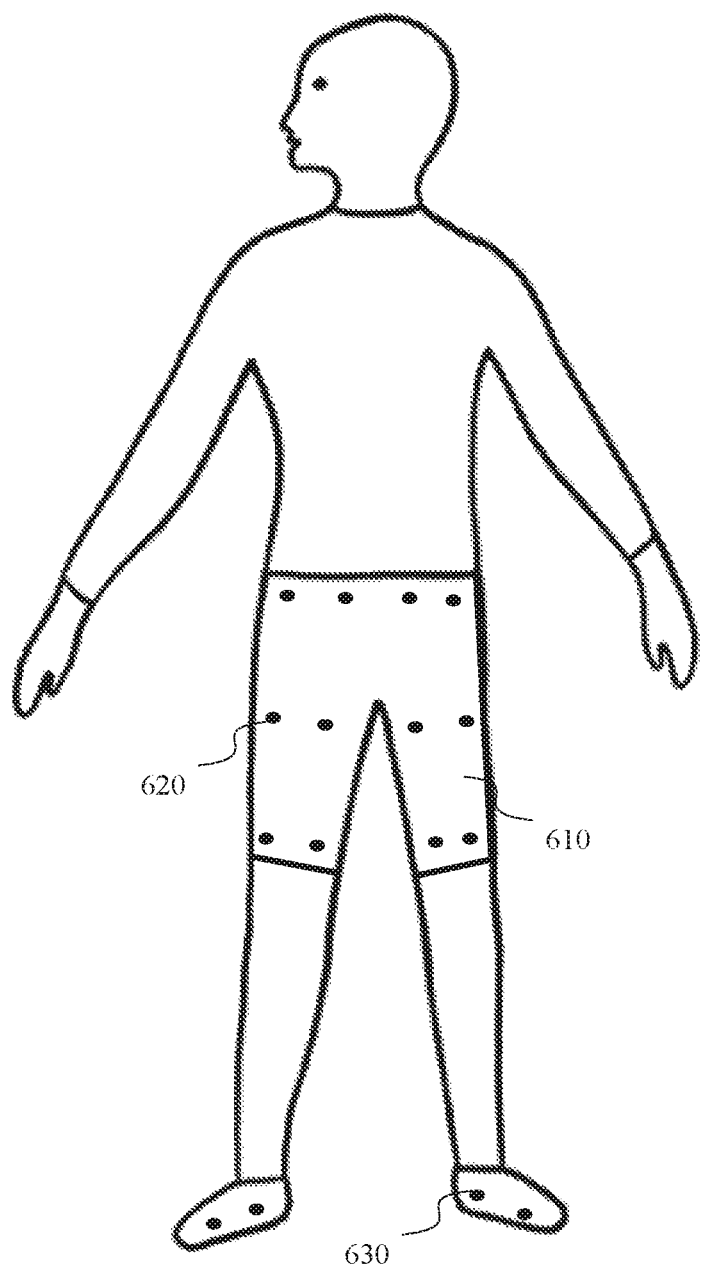
FIG. 6 illustrates an embodiment of an electronic joint monitoring system, according to certain aspects of the present disclosure.

FIG. 6 illustrates an example electronic joint monitoring system, according to certain aspects of the present disclosure. As shown in FIG. 6, the example electronic joint monitoring system may be a wearable device, for example, in the form of a long pair of bicycle-style shorts 610 that extend to the knee, and various sensors 620, such as event detection sensors and position tracking sensors, may be embedded in the pair of bicycle-style shorts 610. For example, multiple acoustic sensors may be embedded at different locations in the pair of bicycle-style shorts 610 to detect a sound generated by the hip joint, determine a location of the origin of the sound, and activate other sensors of the electronic joint monitoring system. In some implementations, the acoustic sensors may be positioned at predefined location on the wearable device. In some implementations, the locations of the acoustic sensors may not be predefined, and may be determined by, for example, calibration devices described below, after the acoustic sensors are attached to a user.

In some embodiments, a position tracking sensor may be embedded in the pair of bicycle-style shorts 610 at a location near the small of the back to determine an approximate location of the hip. A position tracking sensor may be embedded in the pair of bicycle-style shorts 610 at a location near the knee to provide the approximate location of the knee. Based on the outputs from the position tracking sensor near the knee and the position tracking sensor near the small of the back, the relative angular displacement of the joint may be determined to provide a close approximation of the position of the hip. The position tracking sensors may also determine the moving speed, acceleration, and/or orientation of different body parts of the joint based on gravity and the earth's magnetic field using, for example, accelerometers and gyroscopes as described above.

In some embodiments, the example electronic joint monitoring system may include one or more force sensors 630 embedded in, for example, the soles of a pair of shoes to detect and log forces or torques applied to the legs of a patient during daily activities or during medical examinations.

It is noted that the example electronic joint monitoring system shown in FIG. 6 is a specific implementation of the electronic joint monitoring system. The electronic joint monitoring system may be implemented in other forms, such as one or more belts that can be affixed to the waist, thighs, or knees of a patient using, for example, Velcro fasteners or elastic bands.

IV. Calibration Device

As described above, the location of the origin of a snapping sound or other sound may be determined based on the location of each acoustic sensor. Therefore, the accuracy of the determined location of the origin of the sound depends on the accuracy of the locations of the acoustic sensors. In some embodiments, to verify the correct placement or to determine the locations of the acoustic sensors, a calibration device may be used with or included in the electronic joint monitoring system.

Figure 7:
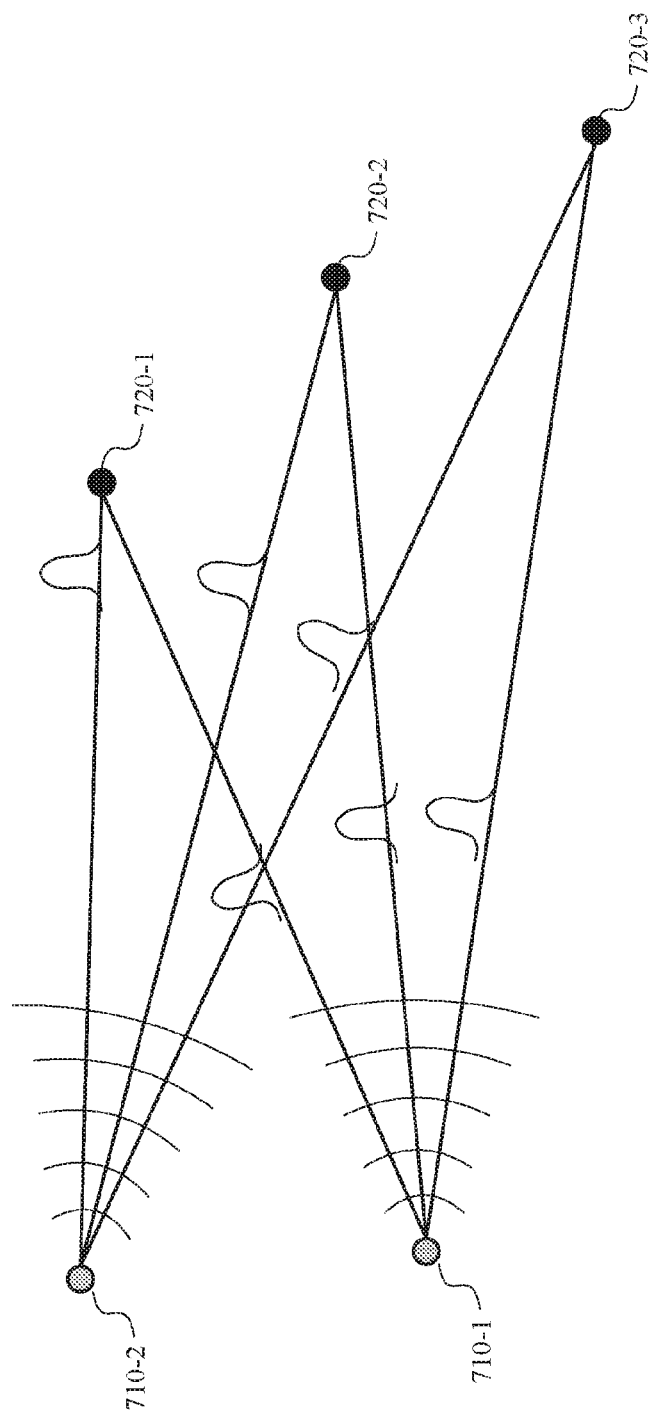
FIG. 7 illustrates an example calibration device, according to certain aspects of the present disclosure.

FIG. 7 illustrates an example calibration device, according to certain aspects of the present disclosure. The calibration device may include one or more transmitters, such as transmitters 710-1 and 710-2. Each of the transmitters may repeatedly transmit acoustic pulses and radio-frequency (RF) pulses. A transmitter may transmit an acoustic pulse (or a series of acoustic pulses) and an RF pulse (or a series of RF pulses) at the same time or after a known time delay. The acoustic pulses may have similar frequency components as the sounds generated by the joint and may be detected by each acoustic sensor, such as acoustic sensor 720-1, 720-2, or 720-3. Each acoustic sensor 720-1, 720-2, or 720-3 may also include an RF detector that can detect the RF pulses transmitted by the transmitters at the same time the acoustic pulses are transmitted or after a known time delay since the acoustic pulses are transmitted. Because an acoustic pulse propagates at a relatively predictable speed in body tissue, and an RF pulse travels effectively instantaneously to each acoustic sensor, the distance between the transmitter 710-1 or 710-2 and each acoustic sensor may be determined based on the delay between the time instants an RF pulse and an acoustic pulse are received by the acoustic sensor if the RF pulse and the acoustic pulse are transmitted at a same time instant. Alternatively, the distance between the transmitter 710-1 or 710-2 and each acoustic sensor may be determined based on the delay between the time instants an RF pulse and an acoustic pulse are received by the acoustic sensor and the delay between the time instants the RF pulse and the acoustic pulse are transmitted by the transmitter. The longer the delay between the time instants the RF pulse and the acoustic pulse are received by the receiving acoustic sensor, the longer the distance between the transmitter of the calibration device and the receiving acoustic sensor.

In some embodiments, the calibration device may include one transmitter for determining a distance from the calibration device to each receiving acoustic sensor. In some embodiments, the calibration device may include two or more transmitters placed in different but known locations to determine the relative 2-dimensional or 3-dimensional location of each acoustic sensor.

In some implementations, the calibration device may be used to verify that each acoustic sensor is in the predetermined location, such that, when a sound is generated by the joint, the location of the source of the sound can be accurately determined using the acoustic sensors. In some implementations, the acoustic sensors may be placed without predetermined locations, and the calibration device may be used to determine the placement locations of the acoustic sensors. In some implementations, the locations of the acoustic sensors may be determined periodically or regularly using the calibration device while the joint is in motion. In some implementations, a similar calibration device may be used to determine the locations of the position tracking sensors.

V. Joint Performance Map

In some implementations, data recorded by the various sensors and stored in the computer-readable storage medium (e.g., a flash memory) during a patient's daily activities or medical examinations for hundreds or more of events associated with snapping sounds or other sounds generated by a joint may be read by a computing system, such as a computer or a mobile device, to generate a two-dimensional or three-dimensional joint map. The joint map may indicate, for example, ranges of motion of the joint, origins of sounds generated by the joint, locations of the joint parts when sounds are generated by the joint, locations of the joint parts when painful events occur, or any combination thereof, during daily activities or medical examinations. The joint map may also include or be correlated with the anatomy of the patient's joint (including bones, muscles, ligaments, tendons, and cartilages) acquired through various medical imaging techniques, such as X-ray, MRI, or CT scan. The map may be a three-dimensional map showing ranges of motion of the joint, origins of sounds generated by the joint, and/or locations of the joint parts when sounds or pains occur in the three-dimensional space as shown in FIG. 2. In some embodiments, the map may include ranges of motion of the joint, origins of sounds generated by the joint, and/or locations of the joint parts in a sagittal, frontal, or transverse plane.

Data collected from the sensors may be used to monitor patient behaviors. For example, remaining in a same position for a long time period may put more stress on joints, tendons, and muscles. The data collected from the sensors may be used to identify behaviors that may worsen the symptoms and to suggest behavior changes to a patient.

The map may be used for diagnosis and treatment of an injured joint. For example, some people may have hypermobile joints that can go beyond an expected range of motion without an injury. Thus, a map with only joint positions recorded during daily activities may not provide sufficient information for diagnosis. On the other hand, a map with joint positions associated with snapping sounds or pains may be more useful for determining the root cause of pains or injuries. For example, the joint map may be correlated with the anatomy of the patient's joint to determine, for example, which bone, tendon, cartilage, muscle, ligament, or other tissue has defects or has been injured based on the detected locations of the origins of sounds generated by the joint.

VI. Example Methods

Figure 8:
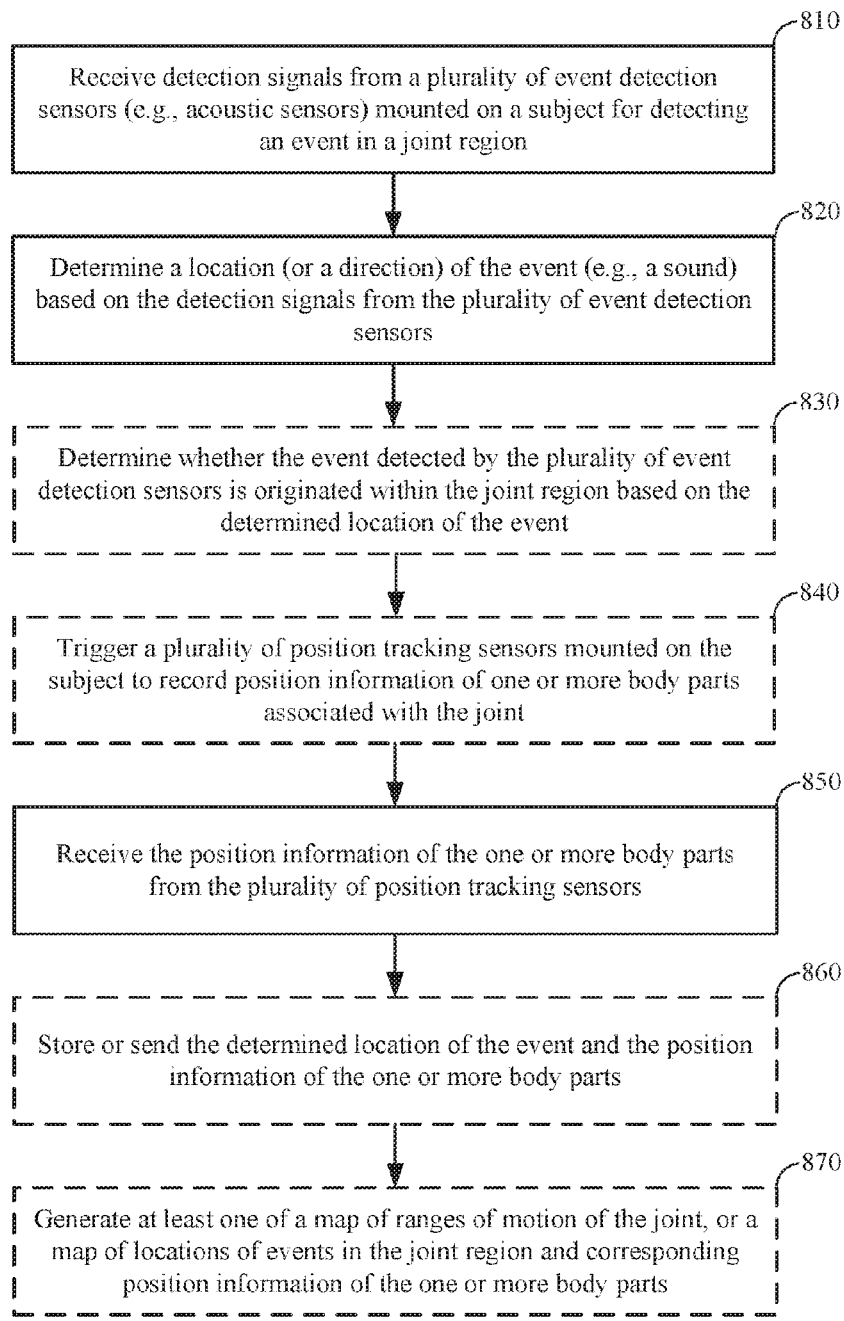
FIG. 8 is a flow chart illustrating an example method for joint performance monitoring and diagnosis, according to certain aspects of the present disclosure.

FIG. 8 is a flow chart 800 illustrating an example method for joint performance monitoring and diagnosis, according to certain aspects of the present disclosure. In various embodiments, some or all operations in flow chart 800 may be performed by, for example, low-power controller 310 in electronic joint monitoring system 300 of FIG. 3, wireless device 900 of FIG. 9 described below, or computing system 1000 of FIG. 10 described below.

At block 810, a controller or a processing unit, such as low-power controller 310 or processing unit 910 of wireless device 900, may receive detection signals from a plurality of event detection sensors (e.g., acoustic sensors 342 of FIG. 3) mounted on a subject (e.g., a wearer of the joint monitoring system) for detecting an event (e.g., a sound) in a joint region, such as the hip region. The joint region may include a region within a body of the wearer and within a threshold distance of a joint, such as the hip joint. The plurality of event detection sensors may be embedded in a pair of shorts or in one or more belts. The plurality of event detection sensors may include, for example, a condenser or capacitive microphone using silicon diaphragms, a piezoelectric acoustic sensor, or an electret microphone. The detection signals may include the amplitude, phase, frequency information of a sound received by the plurality of acoustic sensors.

At block 820, the controller or processing unit may determine a location or a direction of an event (e.g., a sound) detected by the plurality of event detection sensors based on, for example, the amplitude or phase information of the detection signals from the plurality of event detection sensors, as described above with respect to FIGS. 4 and 5. For example, the location of the event may be determined using a trilateration technique, and may be represented by three-dimensional coordinates. The direction of the event, such as a sound, may be determined using an array of acoustic sensors, and may be represented by an angle with respect to a normal direction of the array of synchronized acoustic sensors as shown by θ in FIG. 5.

In some instances, a sound detected by the plurality of acoustic sensors may be a sound originated outside of a body (e.g., a background noise) or outside of a joint region. Optionally, at block 830, the controller or processing unit may determine whether the event detected by the plurality of event detection sensors is originated within a body in a joint region based on the determined location or direction of the event. For example, based on the determined location of a snapping sound and the anatomy of the patient's joint determined using, for example, medical images captured by X-ray, MRI, or CT scan, the corresponding bone, tendon, cartilage, muscle, ligament, or other tissue associated with the joint at the determined location may be determined. In some embodiments, whether the event detected by the plurality of event detection sensors is originated within a body may be determined based on the direction of the snapping sound with respect to an array of acoustic sensors that are mounted on one or more body parts associated with the joint.

Optionally, at block 840, the controller or processing unit may trigger a plurality of position tracking sensors mounted on the wearer to record the position of each of one or more body parts associated with the joint. For example, the plurality of position tracking sensors may be mounted on the small of the back, thighs, or knees of the body. In some embodiments, the controller or processing unit may trigger the plurality of position tracking sensors in response to determining that the event detected by the plurality of event detection sensors is originated within the joint region. No action may be taken if it is determined that the event detected by the plurality of event detection sensors is originated outside of the body or outside of the joint region. In some instances, the controller or processing unit may trigger a plurality of position tracking sensors to record the positional information of the one or more body parts associated with joint based on a user input or user command through a user interface, such as a button or a touch pad. For example, a patient may send a command to the controller to activate the plurality of position tracking sensors when the patient feels a pain. In some embodiments, the position tacking sensors may keep tracking the positions of the one or more body parts, but may only record the position information when an event is detected. In some embodiments, the position tracking sensors may only be activated to determine and record the position information of the one or more body parts when an event is detected.

At block 850, the controller or processing unit may receive position information of the one or more body parts associated with the joint from the plurality of position tracking sensors mounted on the wearer. As described above with respect to FIG. 3, the plurality of position tracking sensors may include, for example, accelerometers, magnetic field sensors, and/or gyroscopes, and may determine their relative or absolute positions using various known methods. In some embodiments, the plurality of position tracking sensors may determine their relative or absolute positions at fixed time intervals. In some embodiments, the plurality of position tracking sensors may determine their relative or absolute positions only when being activated by the controller, or may only record or send the determined positions when being triggered or queried by the controller.

Optionally, at block 860, the controller or processing unit may store (e.g., in a flash memory) or send (e.g., through a wireless transmitter to a mobile device or a cloud server) the determined location of the event and the position information of the one or more body parts.

Optionally, at block 870, a mobile device or a computing system (e.g., a personal computer or a server) may generate at least one of a map of ranges of motion of the joint, or a map of locations of events occurred in the joint region and corresponding position information of the one or more body parts, based on the locations of the events and position information of the one or more body parts associated with the joint stored in a memory or on a server. The map may be used to identify behaviors that may worsen the symptoms and to suggest behavior changes to a patient. The map may also be used for diagnosis and treatment of an injured joint, such as identifying the bone, tendon, cartilage, muscle, ligament, or other tissue that has defects or has been injured.

It is noted that even though FIG. 8 describes the operations as a sequential process, some of the operations may be performed in parallel or concurrently. In addition, the order of the operations may be rearranged. An operation may have additional steps not included in the figure. Some operations may be optional, and thus may be omitted in various embodiments. Some operations described in one block may be performed together with operations described at another block. Additional operations may be added. For example, in some embodiments, the method for joint performance monitoring and diagnosis may also include determining a location of an acoustic sensor of the plurality of acoustic sensors based on the time instants when an acoustic signal and an RF signal generated by a same transmitter of a plurality of transmitters in a calibration device are received by the acoustic sensor. Furthermore, embodiments of the methods may be implemented in hardware, software, firmware, middleware, microcode, hardware description languages, or any combination thereof.

VII. Example Devices and Systems

Figure 9:
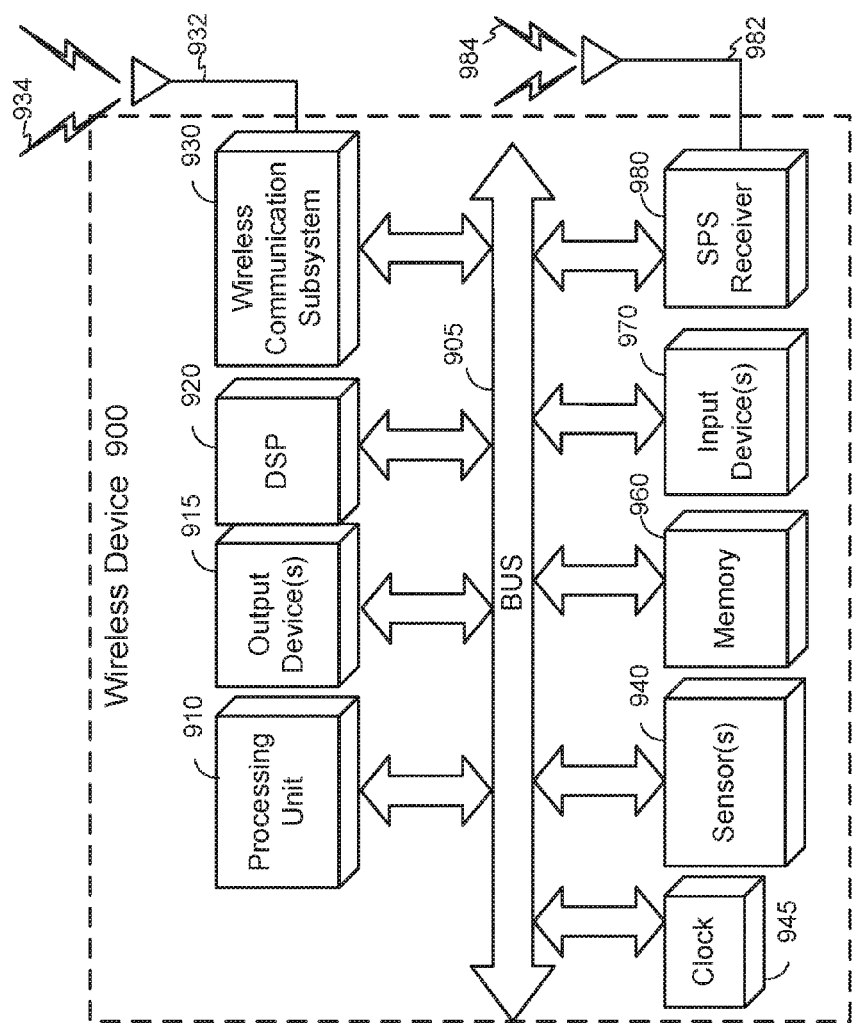
FIG. 9 is a block diagram of an example wireless device for implementing some of the examples described herein.

FIG. 9 illustrates an embodiment of a wireless device 900, which can be utilized as described herein above. For example, wireless device 900 can be used in electronic joint monitoring system 300 or can be used to perform at least some operations described above with respect to FIG. 8. It should be noted that FIG. 9 is meant only to provide a generalized illustration of various components, any or all of which may be utilized as appropriate. It can be noted that, in some instances, components illustrated by FIG. 9 can be localized to a single physical device and/or distributed among various devices, which may be disposed at different physical locations. As such, components may vary from embodiment to embodiment.

Wireless device 900 is shown comprising hardware elements that can be electrically coupled via a bus 905 (or may otherwise be in communication, as appropriate). The hardware elements may include a processing unit(s) 910 which can include without limitation one or more general-purpose processors, one or more special-purpose processors (such as digital signal processing (DSP) chips, graphics acceleration processors, application specific integrated circuits (ASICs), and/or the like), and/or other processing structure or means, which can be configured to perform one or more of the methods described herein, such as determining whether an electrode is at an area of interest. As shown in FIG. 9, some embodiments may have a separate DSP 920, depending on desired functionality. Wireless device 900 also can include one or more input devices 970, which can include without limitation a touch pad, button(s), dial(s), switch(es), and/or the like; and one or more output devices 915, which can include without limitation light emitting diodes (LEDs), speakers, and/or the like.

Wireless device 900 might also include a wireless communication subsystem 930, which can include without limitation a wireless communication device, and/or a chipset (such as a Bluetooth device, an International Electrical and Electronics Engineers (IEEE) 802.11 device (e.g., a device utilizing one or more of the 802.11 standards described herein), an IEEE 802.15.4 device, a WiFi device, a WiMax device, cellular communication facilities, etc.), and/or the like. Wireless communication subsystem 930 may permit data to be exchanged with a network, wireless access points, other computer systems, and/or any other electronic devices described herein, such as a mobile device or a remote controller. The communication can be carried out via one or more wireless communication antenna(s) 932 that send and/or receive wireless signals 934. In various embodiments, wireless communication subsystem 930 may be used to receive commands from a patient to turn on or off the electronic joint monitoring device or activate the position tracking sensors, or to send data to a cloud server or other devices.

Depending on the desired functionality, wireless communication subsystem 930 can include separate transceivers to communicate with antennas of base transceiver stations and other wireless devices and access points as described above, which may include communicating with different data networks and/or network types, such as wireless wide-area networks (WWANs), wireless local area networks (WLANs), or wireless personal area networks (WPANs). A WWAN may be a network using any air interface technology, for example, a code division multiple access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a WiMax (IEEE 802.16), and so on. A CDMA network may implement one or more radio access technologies (RATs) such as cdma2000, W-CDMA, and so on. Cdma2000 includes IS-95, IS-2000, and/or IS-856 standards. A TDMA network may implement GSM, Digital Advanced Mobile Phone System (D-AMPS), or some other RATs. An OFDMA network may employ long-term evolution (LTE), LTE Advanced, and so on. LTE, LTE Advanced, GSM, and W-CDMA are described in documents from 3GPP. Cdma2000 is described in documents from a consortium named "3rd Generation Partnership Project 2" (3GPP2). 3GPP and 3GPP2 documents are publicly available. A WLAN may be an IEEE 802.11x network. A WPAN may be a Bluetooth network, an IEEE 802.15x, or some other type of network.

Wireless device 900 may include a clock 945 on bus 905, which can generate a signal to synchronize various components on bus 905. Clock 945 may include an inductor-capacitor (LC) oscillator, a crystal oscillator, a ring oscillator, a digital clock generator such as a clock divider or clock multiplexer, a phase locked loop, or other clock generator. Clock 945 may be synchronized (or substantially synchronized) with corresponding clocks on other wireless devices for data communication. Clock 945 may be driven by wireless communication subsystem 930, which may be used to synchronize clock 945 of wireless device 900 to one or more other devices. Clock 945 may be used as the time base or reference for synchronizing different sensors or transmitters, generating periodic acoustic or RF pulses, or determining the time a signal is received.

Wireless device 900 can further include sensor(s) 940. Such sensors can include, without limitation, one or more acoustic sensor(s), accelerometer(s), gyroscope(s), camera(s), magnetometer(s), altimeter(s), microphone(s), proximity sensor(s), light sensor(s), and the like. Some or all of sensor(s) 940 can be utilized, among other things, for audio signal detection, motion detection, force detection, environment monitoring, and positioning.

Embodiments of the mobile device may also include a Standard Positioning Service (SPS) receiver 980 capable of receiving signals 984 from one or more SPS satellites using an SPS antenna 982. SPS receiver 980 can extract a position of the mobile device, using conventional techniques, from SPS satellite vehicles (SVs) of an SPS system, such as global navigation satellite system (GNSS) (e.g., Global Positioning System (GPS)), Galileo, Glonass, Compass, Quasi-Zenith Satellite System (QZSS) over Japan, Indian Regional Navigational Satellite System (IRNSS) over India, Beidou over China, and/or the like. Moreover, SPS receiver 980 can use various augmentation systems (e.g., a Satellite Based Augmentation System (SBAS)) that may be associated with or otherwise enabled for use with one or more global and/or regional navigation satellite systems. By way of example but not limitation, an SBAS may include an augmentation system(s) that provides integrity information, differential corrections, etc., such as, e.g., Wide Area Augmentation System (WAAS), European Geostationary Navigation Overlay Service (EGNOS), Multi-functional Satellite Augmentation System (MSAS), GPS Aided Geo Augmented Navigation or GPS and Geo Augmented Navigation system (GAGAN), and/or the like. Thus, as used herein, an SPS system may include any combination of one or more global and/or regional navigation satellite systems and/or augmentation systems, and SPS signals may include SPS, SPS-like, and/or other signals associated with one or more such SPS systems. SPS receiver 980 may be used to determine a geographic location of the electronic joint monitoring system.

Wireless device 900 may further include and/or be in communication with a memory 960. Memory 960 may include any non-transitory storage device, and may include, without limitation, local and/or network accessible storage, a disk drive, a drive array, an optical storage device, a solid-state storage device, such as a random access memory (RAM), and/or a read-only memory (ROM), which can be programmable, flash-updateable, and/or the like. Such storage devices may be configured to implement any appropriate data stores, including without limitation, various file systems, database structures, and/or the like. For instance, memory 960 may include a database (or other data structure) configured to store detected various detection signals, determined locations of the origins of sounds, determined positions of various body parts of a joint, etc.

Memory 960 of wireless device 900 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more procedures described with respect to the functionality discussed above, such as the method shown in FIG. 8 might be implemented as code and/or instructions that can be stored or loaded in memory 960 and be executed by wireless device 900, a processing unit within wireless device 900, and/or another device of a wireless system. In an aspect, such code and/or instructions can be used to configure and/or adapt a general purpose computer (or other device) to perform one or more operations in accordance with the described methods.

Figure 10:
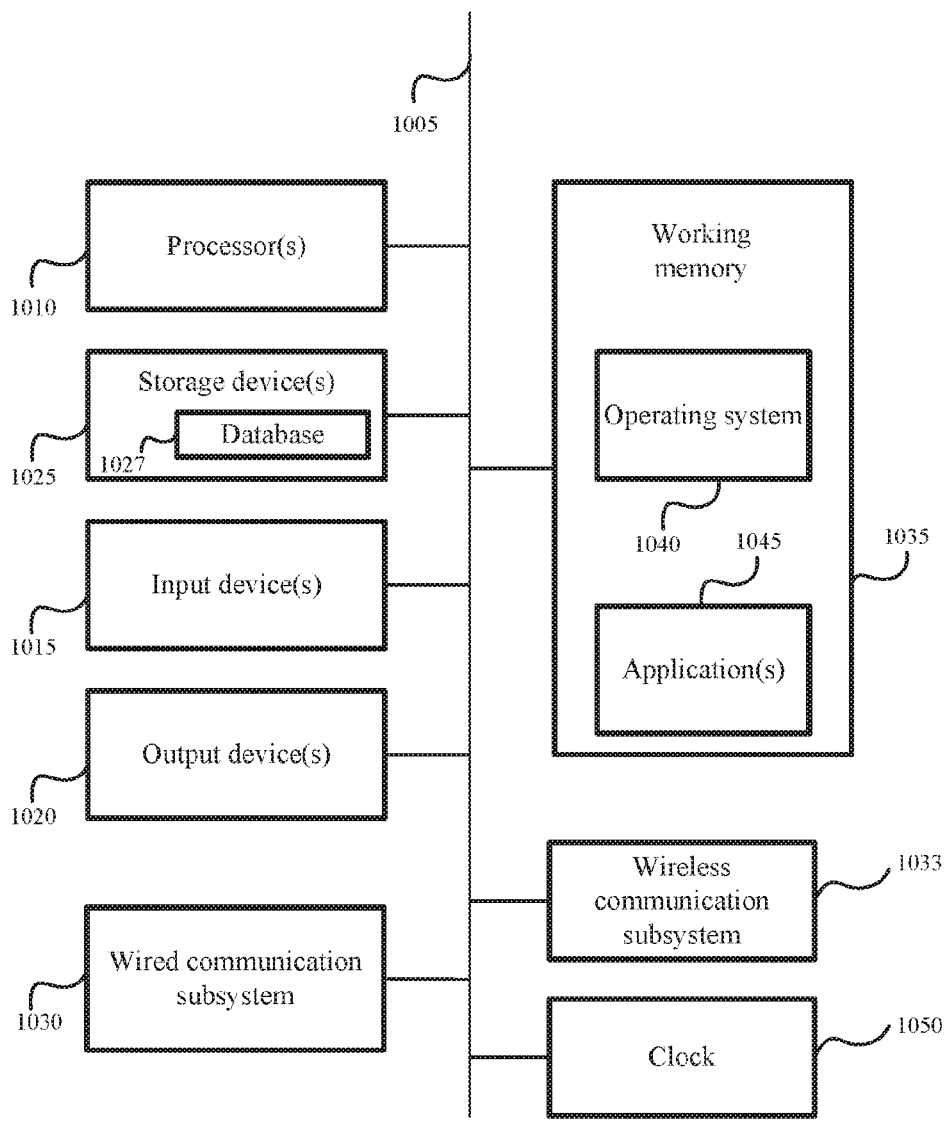
FIG. 10 is a block diagram of an example computing system for implementing some of the examples described herein.

FIG. 10 illustrates components of an example computing system 1000 for implementing some of the examples described herein. For example, computing system 1000 can be used to generate the joint performance map and to perform at least some operations described above with respect to FIG. 8. It should be noted that FIG. 10 is meant only to provide a generalized illustration of various components, any or all of which may be utilized as appropriate. Moreover, system elements may be implemented in a relatively separated or relatively more integrated manner.

Computing system 1000 is shown comprising hardware elements that can be electrically coupled via a bus 1005 (or may otherwise be in communication, as appropriate). The hardware elements may include processor(s) 1010, one or more input devices 1015, and one or more output devices 1020. Input device(s) 1015 can include without limitation camera(s), a touchscreen, a touch pad, microphone(s), a keyboard, a mouse, button(s), dial(s), switch(es), and/or the like. Output devices 1020 may include without limitation a display device, a printer, LEDs, speakers, and/or the like.

Processor(s) 1010 may include without limitation one or more general-purpose processors, one or more special-purpose processors (such as digital signal processing (DSP)

chips, graphics acceleration processors, application-specific integrated circuits (ASICs), and/or the like), and/or other processing structures or means, which can be configured to perform one or more of the methods described herein.

Computing system 1000 can also include a wired communication subsystem 1030 and a wireless communication subsystem 1033. Wired communication subsystem 1030 and wireless communication subsystem 1033 can include, without limitation, a modem, a network interface (wireless, wired, both, or other combination thereof), an infrared communication device, a wireless communication device, and/or a chipset (such as a Bluetooth™ device, an International Electrical and Electronics Engineers (IEEE) 802.11 device, e.g., a device utilizing one or more of the IEEE 802.11 standards described herein), a WiFi device, a WiMax device, cellular communication facilities, etc.), and/or the like. Subcomponents of the network interface may vary, depending on the type of computing system 1000. Wired communication subsystem 1030 and wireless communication subsystem 1033 may include one or more input and/or output communication interfaces to permit data to be exchanged with a data network, wireless access points, other computer systems, and/or any other devices described herein.

Depending on desired functionality, wireless communication subsystem 1033 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 802.16) network. A WLAN may be, for example, an IEEE 802.11x network. A WPAN may be, for example, a Bluetooth network, an IEEE 802.15x, or some other types of network. The techniques described herein may also be used for any combination of WWAN, WLAN, and/or WPAN.

Computing system 1000 of FIG. 10 may include a clock 1050 on bus 1005, which can generate a signal to synchronize the various components on bus 1005. Clock 1050 may include an LC oscillator, a crystal oscillator, a ring oscillator, a digital clock generator such as a clock divider or clock multiplexer, a phase locked loop, or other clock generator. The clock may be synchronized (or substantially synchronized) with corresponding clocks on other devices while performing the techniques described herein.

Computing system 1000 may further include (and/or be in communication with) one or more non-transitory storage devices 1025, which can comprise, without limitation, local and/or network accessible storage, and/or can include, without limitation, a disk drive, a drive array, an optical storage device, a solid-state storage device, such as a random access memory (RAM), and/or a read-only memory (ROM), which can be programmable, flash-updateable, and/or the like. Such storage devices may be configured to implement any appropriate data stores, including, without limitation, various file systems, database structures, and/or the like. For instance, storage device(s) 1025 may include a database 1027 (or other data structure) configured to store various detection signals, determined locations of the origins of sounds, determined positions of various body parts of a joint, etc., as described in embodiments herein.

In many embodiments, computing system 1000 may further comprise a working memory 1035, which can include a RAM or ROM device, as described above. Software elements, shown as being currently located within working memory 1035, can include an operating system 1040, device drivers, executable libraries, and/or other code, such as one or more application programs 1045, which may comprise software programs provided by various embodiments, and/or may be designed to implement methods, and/or configure systems, provided by other embodiments, as described herein, such as some or all of the methods described in relation to FIG. 8. Merely by way of example, one or more procedures described with respect to the method discussed above might be implemented as code and/or instructions executable by a computer (and/or a processor within a computer). In an aspect, such code and/or instructions can be used to configure and/or adapt a general-purpose computer (or other device) to perform one or more operations in accordance with the described methods.

A set of these instructions and/or code might be stored on a non-transitory computer-readable storage medium, such as non-transitory storage device(s) 1025 described above. In some cases, the storage medium might be incorporated within a computer system, such as computing system 1000. In other embodiments, the storage medium might be separate from a computer system (e.g., a removable medium, such as a flash drive), and/or provided in an installation package, such that the storage medium can be used to program, configure, and/or adapt a general purpose computer with the instructions/code stored thereon. These instructions might take the form of executable code, which is executable by computing system 1000 and/or might take the form of source and/or installable code, which, upon compilation and/or installation on computing system 1000 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The terms "machine-readable medium" and "computer-readable medium" as used herein refer to any storage medium that participates in providing data that causes a machine to operate in a specific fashion. In embodiments provided hereinabove, various machine-readable media might be involved in providing instructions/code to processors and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media, punch cards, paper tape, any other physical medium with patterns of holes, a RAM, a programmable read-only memory (PROM), an erasable programmable read-only memory (EPROM), a FLASH-EPROM, any other memory chip or cartridge, a carrier wave as described hereinafter, or any other medium from which a computer can read instructions and/or code.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

It has proven convenient at times, principally for reasons of common usage, to refer to such signals as bits, information, values, elements, symbols, characters, variables, terms, numbers, numerals, or the like. It should be understood, however, that all of these or similar terms are to be associated with appropriate physical quantities and are merely convenient labels. Unless specifically stated otherwise, as is apparent from the discussion above, it is appreciated that throughout this specification discussions utilizing terms such as "processing," "computing," "calculating," "determining," "ascertaining," "identifying," "associating," "measuring," "performing," or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic, electrical, or magnetic quantities within memories, registers, or other information storage devices, transmission devices, or display devices of the special purpose computer or similar special purpose electronic computing device.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms "and," "or," and "an/or," as used herein, may include a variety of meanings that also is expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, B, C, AB, AC, BC, AA, AAB, ABC, AABBCCC, etc.

Reference throughout this specification to "one example," "an example," "certain examples," or "exemplary implementation" means that a particular feature, structure, or characteristic described in connection with the feature and/or example may be included in at least one feature and/or example of claimed subject matter. Thus, the appearances of the phrase "in one example," "an example," "in certain examples," "in certain implementations," or other like phrases in various places throughout this specification are not necessarily all referring to the same feature, example, and/or limitation. Furthermore, the particular features, structures, or characteristics may be combined in one or more examples and/or features.

Some portions of the detailed description included herein may be presented in terms of algorithms or symbolic representations of operations on binary digital signals stored within a memory of a specific apparatus or special purpose computing device or platform. In the context of this particular specification, the term specific apparatus or the like includes a general-purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining," or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

In the preceding detailed description, numerous specific details have been set forth to provide a thorough understanding of claimed subject matter. However, it will be understood by those skilled in the art that claimed subject matter may be practiced without these specific details. In other instances, methods and apparatuses that would be known by one of ordinary skill have not been described in detail so as not to obscure claimed subject matter. Therefore, it is intended that claimed subject matter not be limited to the particular examples disclosed, but that such claimed subject matter may also include all aspects falling within the scope of appended claims, and equivalents thereof.

For an implementation involving firmware and/or software, the methodologies may be implemented with modules (e.g., procedures, functions, and so on) that perform the functions described herein. Any machine-readable medium tangibly embodying instructions may be used in implementing the methodologies described herein. For example, software codes may be stored in a memory and executed by a processor unit. Memory may be implemented within the processor unit or external to the processor unit. As used herein the term "memory" refers to any type of long term, short term, volatile, nonvolatile, or other memory and is not to be limited to any particular type of memory or number of memories, or type of media upon which memory is stored.

If implemented in firmware and/or software, the functions may be stored as one or more instructions or code on a computer-readable storage medium. Examples include computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, compact disc read-only memory (CD-ROM) or other optical disk storage, magnetic disk storage, semiconductor storage, or other storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

In addition to storage on computer-readable storage medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims. That is, the communication apparatus includes transmission media with signals indicative of information to perform disclosed functions. At a first time, the transmission media included in the communication apparatus may include a first portion of the information to perform the disclosed functions, while at a second time the transmission media included in the communication apparatus may include a second portion of the information to perform the disclosed functions.

What is claimed is:

1. A joint monitoring system comprising:
   a plurality of event detection sensors configured to be mounted on a wearer of the joint monitoring system and configured to generate detection signals for detecting an event in a joint region, wherein the detection signals from the plurality of event detection sensors comprise information for determining a location of the event, and wherein the joint region comprises a region within a body of the wearer and within a threshold distance of a joint; and
   a plurality of position tracking sensors configured to be mounted on the wearer and configured to, in response to the detected event, record position information of one or more body parts associated with the joint.

2. The joint monitoring system of claim 1, further comprising a controller configured to execute instructions to determine the location of the event based on the detection signals from the plurality of event detection sensors.

3. The joint monitoring system of claim 2, further comprising a computer-readable storage medium configured to store the position information of the one or more body parts and the determined location of the event.

4. The joint monitoring system of claim 2, further comprising a wireless communication subsystem configured to send the position information of the one or more body parts and the determined location of the event to an external device.

5. The joint monitoring system of claim 2, wherein the controller is configured to execute instructions to detect the event based on the detection signals from the plurality of event detection sensors and one or more threshold values.

6. The joint monitoring system of claim 2, wherein the controller is further configured to execute instructions to:
   determine that the event detected by the plurality of event detection sensors is originated within the joint region based on the determined location of the event; and
   in response to determining that the event detected by the plurality of event detection sensors is originated within the joint region, trigger the plurality of position tracking sensors to record the position information of the one or more body parts.

7. The joint monitoring system of claim 1, wherein:
   the plurality of event detection sensors comprises a plurality of acoustic sensors; and
   the event comprises a sound.

8. The joint monitoring system of claim 7, further comprising a controller, wherein:
   the plurality of acoustic sensors includes an array of acoustic sensors; and
   the controller is configured to execute instructions to determine a direction of the sound based on the detection signals from the array of acoustic sensors.

9. The joint monitoring system of claim 8, wherein the controller is further configured to execute instructions to:
   determine that the sound is originated within the joint region based on the determined direction of the sound; and
   in response to determining that the sound is originated within the joint region, trigger the plurality of position tracking sensors to record the position information of the one or more body parts.

10. The joint monitoring system of claim 1, wherein the plurality of position tracking sensors comprises an accelerometer, a gyroscope, a magnetic field sensor, or any combination thereof.

11. The joint monitoring system of claim 1, wherein the position information of each of the one or more body parts comprises a position of each of the one or more body parts or data for determining the position of each of the one or more body parts.

12. The joint monitoring system of claim 1, further comprising a user interface, wherein the plurality of position tracking sensors is configured to, in response to an input signal from the user interface, record the position information of the one or more body parts.

13. The joint monitoring system of claim 12, wherein the input signal from the user interface indicates that a pain has occurred in the joint region.

14. The joint monitoring system of claim 1, further comprising:
   a calibration device comprising a transmitter, the transmitter configured to generate an acoustic signal and a radio-frequency (RF) signal,
   wherein a first event detection sensor of the plurality of event detection sensors is configured to receive the RF signal at a first time instant and receive the acoustic signal at a second time instant, a time delay between the first time instant and the second time instant indicating a distance between the transmitter of the calibration device and the first event detection sensor.

15. The joint monitoring system of claim 14, further comprising a controller, wherein:

the calibration device comprises two or more transmitters, each transmitter of the two or more transmitters configured to generate an acoustic signal and an RF signal;

the first event detection sensor is configured to receive the RF signal and the acoustic signal generated by each of the two or more transmitters; and the controller is configured to determine a location of the first event detection sensor based on time instants when the RF signal and the acoustic signal generated by each of the two or more transmitters are received by the first event detection sensor.

16. The joint monitoring system of claim 1, wherein the plurality of event detection sensors and the plurality of position tracking sensors are embedded in an article of clothing.

17. The joint monitoring system of claim 1, further comprising a force sensor configured to be affixed to a shoe, the force sensor configured to detect a force applied to a leg.

18. A method for monitoring a joint, the method comprising:

receiving detection signals from a plurality of event detection sensors mounted on a subject for detecting an event in a joint region, the joint region comprising a region within a body of the subject and within a threshold distance of the joint;

determining a location of the event based on the detection signals from the plurality of event detection sensors; and receiving position information of one or more body parts associated with the joint from a plurality of position tracking sensors mounted on the subject, wherein the position information is recorded by the plurality of position tracking sensors in response to the detected event.

19. The method of claim 18, further comprising:

determining that the event detected by the plurality of event detection sensors is originated within the joint region based on the determined location of the event; and in response to determining that the event detected by the plurality of event detection sensors is originated within the joint region, triggering the plurality of position tracking sensors to record the position information of the one or more body parts.

20. The method of claim 18, further comprising:

storing the determined location of the event and the position information of the one or more body parts in a computer-readable storage medium.

21. The method of claim 20, further comprising:

generating at least one of a map of ranges of motion of the joint, or a map of locations of events occurred in the joint region and corresponding position information of the one or more body parts associated with the joint, based on the determined location of the event and the position information of the one or more body parts stored in the computer-readable storage medium.

22. The method of claim 18, further comprising:

sending, using a wireless communication subsystem, the determined location of the event and the position information of the one or more body parts to an external device.

23. The method of claim 18, wherein:

the event comprises a sound;

the plurality of event detection sensors comprises a plurality of acoustic sensors; and determining the location of the event comprises determining a direction of the sound based on the detection signals from the plurality of acoustic sensors.

24. The method of claim 18, further comprising:

receiving a user input signal from a user interface; and in response to receiving the user input signal, recording the position information of the one or more body parts.

25. The method of claim 18, further comprising:

determining a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

26. An apparatus comprising:

means for receiving detection signals from a plurality of event detection sensors mounted on a subject for detecting an event in a joint region, the joint region comprising a region within a body of the subject and within a threshold distance of a joint;

means for determining a location of the event based on the detection signals from the plurality of event detection sensors; and means for receiving position information of one or more body parts associated with the joint from a plurality of position tracking sensors mounted on the subject, wherein the position information is recorded by the plurality of position tracking sensors in response to the detected event.

27. The apparatus of claim 26, further comprising:

means for determining that the event detected by the plurality of event detection sensors is originated within the joint region based on the determined location of the event; and means for, in response to determining that the event detected by the plurality of event detection sensors is originated within the joint region, triggering the plurality of position tracking sensors to record the position information of the one or more body parts.

28. The apparatus of claim 26, further comprising:

means for storing or sending the determined location of the event and the position information of the one or more body parts.

29. The apparatus of claim 26, further comprising:

means for determining a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

30. A non-transitory computer-readable storage medium comprising machine-readable instructions stored thereon, the instructions, when executed by one or more processing units, causing the one or more processing units to:

receive detection signals from a plurality of event detection sensors mounted on a subject for detecting an event in a joint region, the joint region comprising a region within a body of the subject and within a threshold distance of a joint;

determine a location of the event based on the detection signals from the plurality of event detection sensors; and receive position information of one or more body parts associated with the joint from a plurality of position tracking sensors mounted on the subject, wherein the position information is recorded by the plurality of position tracking sensors in response to the detected event.

31. The non-transitory computer-readable storage medium of claim 30, wherein the instructions, when executed by the one or more processing units, further cause the one or more processing units to:
   determine that the event detected by the plurality of event detection sensors is originated within the joint region based on the determined location of the event; and
   in response to determining that the event detected by the plurality of event detection sensors is originated within the joint region, trigger the plurality of position tracking sensors to record the position information of the one or more body parts.

32. The non-transitory computer-readable storage medium of claim 31, wherein the instructions, when executed by the one or more processing units, further cause the one or more processing units to:
   determine a location of an event detection sensor of the plurality of event detection sensors based on a time delay between a first time instant when an RF signal generated by a calibration device is received by the event detection sensor and a second time instant when an acoustic signal generated by the calibration device is received by the event detection sensor.

\* \* \* \* \*